United States Patent

Foulkes et al.

[11] Patent Number: 5,567,153
[45] Date of Patent: Oct. 22, 1996

[54] TRANSDUCER ACTIVATED TOOL TIP

[75] Inventors: Harvey B. Foulkes, Commack; George E. Warrin, North Merrick; Huy-Can Dao, Linden; Rene Perdreaux, Brooklyn, all of N.Y.

[73] Assignee: Dentsply Research & Development Corp., Milford, Del.

[21] Appl. No.: 296,296

[22] Filed: Aug. 25, 1994

[51] Int. Cl.⁶ .................................................. A61C 17/02
[52] U.S. Cl. .............................................. 433/119; 433/86
[58] Field of Search ................................... 433/80, 81, 86, 433/104, 119; 76/101.1; 15/250.01

[56] References Cited

U.S. PATENT DOCUMENTS

| | | |
|---|---|---|
| Re. 30,536 | 3/1981 | Perdreaux, Jr. ............. 433/86 |
| D. 261,932 | 11/1981 | Bussiere . |
| 3,076,904 | 2/1963 | Kleesattel et al. . |
| 3,124,878 | 3/1964 | Bodine, Jr., et al. . |
| 3,368,280 | 2/1968 | Friedman et al. . |
| 3,488,851 | 1/1970 | Haydu . |
| 3,518,766 | 7/1970 | Burt . |
| 3,589,012 | 6/1971 | Richman . |
| 3,593,425 | 7/1971 | Robinson . |
| 3,645,255 | 2/1972 | Robinson . |
| 3,654,502 | 4/1972 | Carmona et al. ............. 433/86 X |
| 3,703,037 | 11/1972 | Robinson . |
| 3,924,335 | 12/1975 | Balamuth et al. . |
| 3,930,173 | 12/1975 | Banko ............. 433/119 X |
| 3,956,826 | 5/1976 | Perdreaux, Jr. ............. 433/86 |
| 4,048,723 | 9/1977 | Thorup . |
| 4,169,984 | 10/1979 | Parisi . |
| 4,260,380 | 4/1981 | Nash ............. 433/119 |
| 4,276,880 | 7/1981 | Malmin ............. 433/80 X |
| 4,283,175 | 8/1981 | Nash ............. 433/119 |
| 4,315,742 | 2/1982 | Nash et al. ............. 433/86 |
| 4,332,558 | 6/1982 | Lustig ............. 433/119 X |
| 4,370,131 | 1/1983 | Banko ............. 433/119 X |
| 4,634,376 | 1/1987 | Mössle et al. ............. 433/29 |
| 4,820,152 | 4/1989 | Warrin et al. ............. 433/86 |
| 5,082,443 | 1/1992 | Löhn ............. 433/80 |
| 5,125,837 | 6/1992 | Warrin et al. ............. 433/86 X |
| 5,190,456 | 2/1993 | Hasegawa ............. 433/120 |

FOREIGN PATENT DOCUMENTS

| | | |
|---|---|---|
| 2566262 | 12/1985 | France . |
| 3032022 | 3/1982 | Germany . |

OTHER PUBLICATIONS

Unisonic Transistorized Ultrasonic Scaler, Precision Research Corp. (1968).
The Dentsply-Cavitron Powermatic Ultrasonic Dental Unit, Dentsply International (1976).

*Primary Examiner*—Robert P. Swiatek
*Attorney, Agent, or Firm*—James B. Bieber; Dale R. Lovercheck

[57] ABSTRACT

A transducer activated tool for contacting workpiece surfaces and directing fluid adjacent to the surfaces is disclosed. The tool may be ultrasonically activated by attachment to an insert that includes a magnetostrictive element. The tip includes distal surfaces shaped to contact the workpiece and additionally includes a fluid passageway internal to the tip that is bored generally along the centerline of the tip but is offset from the tip axis such that a discharge orifice is formed in the tip displaced from the distal tip end. The passageway is preferably angularly offset so that the discharge orifice is formed in the distal end of the tip about 2–8 mm from the distal end of the tip. The tip when shaped to conform to dental or tooth surfaces is particularly useful as a dental tool. In another embodiment the fluid passageway is eccentrically offset from the tip axis wherein the passageway is substantially parallel to the center axis but displaced therefrom preferably by about 0.1 to 0.5 mm. The tip end and fluid delivery passageway discharge orifice are located relative to each other such that fluid is provided to the workpiece or tip without the formation of excessive spray and without weakening the distal tip such that it is sufficiently strong to provide useful service in resisting flexural stresses and the like.

33 Claims, 5 Drawing Sheets

Fig. 8

TRANSDUCER ACTIVATED TOOL TIP

BACKGROUND OF THE INVENTION

The invention relates to a transducer activated tool for contacting workpiece surfaces and directing a fluid adjacent to the workpiece. More particularly, the invention relates to an ultrasonically activated tool such as a dental instrument or insert therefore, including a vibrating tip for contacting tooth surfaces. The tip includes a conduit or passageway for directing a fluid onto the dental or tip surfaces.

Many useful dental instruments employ substantial vibratory motion at a tool tip of the instrument for cleaning, scaling and like operations. The tool tips are designed to produce flexural and longitudinal vibrations with flexural motions of from about 0.02 to 0.2 mm. The tip is typically attached to an electro-mechanical part or section that can be induced to vibrate at high frequency. The instrument is driven by an electronic generator at relatively high frequencies, typically on the order of above 20 kHz, to obtain adequate motion and to minimize objectionable noise since the human hearing threshold is about 18 kHz. The energy generator and related electro-mechanical section may be any one of several types such as electro-dynamic, piezo electric, or magnetostrictive. Design of the tip and its related electro-mechanical components involves combining a number of parameters to produce mechanical resonances (harmonic vibrations) at the driving frequency to produce amplified mechanical motion, particularly at the distal tip end.

In many operations employing a vibrating tip tool, it is useful and often necessary to have a source of water or other fluid impinging upon the workpiece surfaces and/or tool surfaces in order to cool them or remove debris generated by the work. For example, in dental applications, when an ultrasonically vibrated tip contacts a tooth surface, as required for performing a cleaning operation, the moving tip against the tooth surface produces heat. The patient may experience a pain sensation which can be severe if the operator applies even mild pressure against the tooth while cleaning. Water or some other fluid is usually supplied to the tooth surface in order to remove the heat and minimize pain and possible heat damage to the tooth. In addition, a number of the electro-mechanical devices utilized in providing a vibrating tip generate heat internally during operation.

An example of an ultrasonic dental tool, wherein a handpiece containing a coil applies an electro-magnetic field to a magnetostrictive insert body to which a tool tip is fixed is described by Perdreaux in U.S. Pat. No. Re. 30,536 (Cavitron). In the Perdreaux design, heat caused by electrical and mechanical friction losses within the tool during vibration are dissipated by means of a cooling fluid that flows axially with respect to the tool insert, over the active magnetostrictive element or stack, emerging from an annular space between the insert and the handpiece and being directed toward the working end of the tool. The Cavitron arrangement is such that heat generated by the insert body warms the fluid which is then directed, as a convenient source of irrigating, flushing and/or cooling fluid, onto the active tip or workpiece area. The warm fluid minimizes reactions by patients who have sensitivity to cold temperatures.

In a number of dental operations, the vibrating tip is guided over and about tooth surfaces by the operator. The tip must be capable of penetrating between teeth and under or below the gingiva or gum line. Generally, the tip must be small in cross-section, ideally having a pointed tip with a tapered cross-section extending about 2.5 to 5 mm back from the distal tip end to allow adequate access between teeth and gingiva.

In addition, the tip is universally curved or shaped to conform to or be compatible with tooth surfaces. Useful tips will curve sufficiently to permit spanning the tooth frontal surface when entrance to abutting surfaces is needed or when access to subgingival zones about the oral cavity are required.

Experience in using such ultrasonically activated and irrigated tips has demonstrated that a combination of tip shape and fluid delivery system must be selected such that the tip is strong enough to support vibrating motion stresses at useable amplitudes. The forming process must be such that minute fractures or other weak points are not introduced into the tip material that might become focal points of breakage during use.

A number of vibrating tools, generally similar to the Perdreaux tool, as described above, are now in dental, medical, veterinary and other uses. These tools employ various designs for directing water or another fluid adjacent to or onto the surfaces being worked upon, as a means of cooling workpiece surfaces and removing debris from the workpiece. For example, a number of ultrasonically activated tools employ separate fluid conduits, external to the instrument itself, for conducting water and other fluids adjacent the tip or onto the workpiece or tip. Kleesattel et al in U.S. Pat. No. 3,076,904 employ a capillary, run externally to the handpiece, with a nozzle formed of a bendable metal extending very near the tip for directing water onto the dental surfaces being worked upon. A difficulty with such arrangements is that the capillary may obstruct free use of the tool tip.

A number of ultrasonic tool tips include internal fluid passageways bored along the longitudinal center axis of the tip component or body. In many such tips, a fluid discharge orifice is formed at the distal end of the tool, for directing fluid onto the workpiece. Such tip design is described, for example, by Balamuth et al in U.S. Pat. No. 3,924,335 for a piezo electric crystal vibrated dental tool. A difficulty in employing this tip design, is that the tip must generally be of a relatively large diameter, on the order of greater than 1 mm, in order to have a sufficiently strong tip and a passageway that provides an adequate flow of fluid. Such a tip may be too blunt for many dental uses as it does not allow adequate tapering such that the tool thus cannot penetrate small inter-tooth spaces and can damage gums when used subgingivally.

Many tips having internal central axial passageways that include a fluid discharge orifice formed by removing a longitudinal lateral portion of the cylindrical wall of the tip as the distal tip end is approached, as shown in Haydu U.S. Pat. No. 3,488,851 and Richman U.S. Pat. No. 3,589,012, for example. In Banko U.S. Pat. No. 3,930,173, Robinson U.S. Pat. No. 3,703,037 and Warrin U.S. Pat. No. 5,125,837, the tip is cut away such that remaining lateral walls of the distal tip form a channel for helping direct water discharging from the center axis bore onto the workpiece.

A difficulty with these cutaway designs is that the remaining partially hollowed out end of the tip can be a rather fragile shell that cannot support adequate vibrational motion without danger of fracturing. Also, the smaller remaining working surfaces of the tip are subject to more rapid erosion resulting in a shorter useful life of the tool tip than desired.

All of the tips that discharge fluid from the distal end of the tip or close thereto are discharging from a tip at or before a point of high flexural motion, which motion often causes the fluid at this point to spray or form a mist adjacent to the tip and workpiece. Such spraying and misting may prevent fluid from reaching the workpiece area and, instead, dispense it over a relatively wide area, including onto the patient and operator.

Thus, the fluid dispensing characteristics associated with the tips heretofore known in the art are generally deficient due to excessive spray and mist formation that discomfort patients and operators as well as obscuring the working surfaces. In addition, the internal fluid passageway discharge orifices tend to weaken tip surfaces, particularly at the distal end of the tip, causing early failure of the tips through fracture and excessive wear. Tips having axial discharge orifices at the distal end of the tip require significantly more metal at the tip, resulting in blunter tools having less usefulness than desired when contacting confined, smaller surfaces, particularly in dental applications.

It is evident from the state of the art that a new tip design for use in vibratory activated tools would be desirable that can supply an adequate flow of cooling/cleaning fluid to the workpiece without excessive spray and provide an internal passageway and exiting orifice such that the resulting tool tip is capable of withstanding necessary flexural motion of the tip without fracture.

SUMMARY OF THE INVENTION

The invention comprises a transducer activated tool for contacting workpiece surfaces and directing a fluid adjacent or onto said surfaces, comprising an activated tip having distal surfaces shaped to contact the workpiece surfaces. The tip additionally includes, in combination, a fluid passageway internal to the tip, generally along the longitudinal center axis of the tip, but offset such that a fluid discharge orifice is formed displaced from the distal tip axis. A connecting body connects said tip to an activating transducer and a fluid source is connected to the tip fluid passageway, providing a flow of fluid discharging from the tip fluid passageway orifice. The distal end of the tip is shaped or bent to form curved surfaces to contact workpiece surfaces, with the tip fluid discharge orifice located such that said fluid impinges upon the workpiece surfaces.

In a preferred embodiment, the tip fluid passageway is angularly offset from the tip longitudinal center axis such that the fluid discharge orifice is formed in a lateral surface of the tip such that the orifice center axis is located about 0.01 to about 8 mm from the distal end of said tip. In a most preferred embodiment, wherein the tip is a component of a dental tool, the fluid discharge orifice is located about 5.5–6.5 mm from the distal end of the tip. The tip includes a curved shape that depends upon its use and, most preferably, is of a universal shape useful in dental operations, having a distal portion bending from its centerline axis through an arc of about 60°–70° degrees. The tool may be activated by sonic, ultrasonic, fluid or air means. The fluid delivered may be any fluid useful for the particular end use in which the tool is employed and is typically a saline solution, water or a solution comprising a medicament. The tool is particularly useful in dental, medical and veterinary uses. A preferred use of the tool is in dental operations such as cleaning, scaling, etc. A preferred tool tip is a component of an insert that is activated by an ultrasonic energy generator means. A preferred ultrasonically activated tool insert comprises a magnetostrictive element; a connecting body axially connected to said magnetostrictive element; and a tip, axially attached to the connecting body, said tip having distal surfaces shaped to contact a workpiece, typically dental surfaces. In combination, the tip includes a fluid passageway internal to the tip, generally along the center axis of the tip, but offset from said axis such that a discharge orifice formed in said tip is displaced from the distal tip end center axis. In a preferred insert, the passageway is angularly offset from the tip axis by less than about 3 degrees such that the orifice exits within the range of 2–8 mm from the distal end of the tip. The insert is particularly useful for cleaning or scaling of teeth, and other dental procedures and, in such service, the distal end is typically bent through an arc of about 60°–70° degrees.

The invention includes a method of making the tip, comprising machining or boring a passageway into a cylindrical rod, beginning at the center axis of an end of the rod and continuing at an angle of less than about 3 degrees from the center axis of said rod such that the passageway forms a discharge orifice 2–8 mm from the opposite distal end of the rod. A preferred method of forming the liquid passageway and discharge orifice is by means of electrical discharge machining. The bored cylindrical rod is then formed into a desired tip shape for contacting the desired workpiece surfaces such as, for example, tooth surfaces. The cylindrical rod may, optionally, be formed into a tapered tip or profile before being pierced, machined, bored or drilled for its internal fluid passageway.

The tip fluid passageway orifice may be offset eccentric to the tip axis, wherein the passageway is bored substantially parallel to the center axis of the tip but displaced from the axis by 0.1 to 0.5 mm.

DETAILED DESCRIPTION OF PREFERRED EMBODIMENTS

The invention is, in general, a transducer activated tool for contacting workpiece surfaces and directing a fluid onto the workpiece. A principal element of the invention is an activated tip comprising distal surfaces that are shaped to contact the workpiece surfaces. Additionally, the tip includes a fluid passageway internal to the tip extending substantially along the longitudinal center axis of the tip but offset such that a fluid discharge orifice is formed displaced from the distal tip axis. A connecting body connects the tip to an activating transducer and a fluid source is connected to the tool to supply a flow of fluid through the fluid passageway such that it discharges from the passageway orifice.

A key advantage of the activated tip of the invention is that the fluid passageway and its discharge orifice arrangement relate to the distal end of the tip such that the arrangement does not weaken the tip distal portion by removing metal or materials of construction at a critical portion of the tip at its point of maximum motion. Secondly, the fluid discharge orifice of the arrangement of the invention is located at or near a node of flexural motion and not near a flexural loop such that spray or mist generation at the orifice is minimized.

Figure 1:
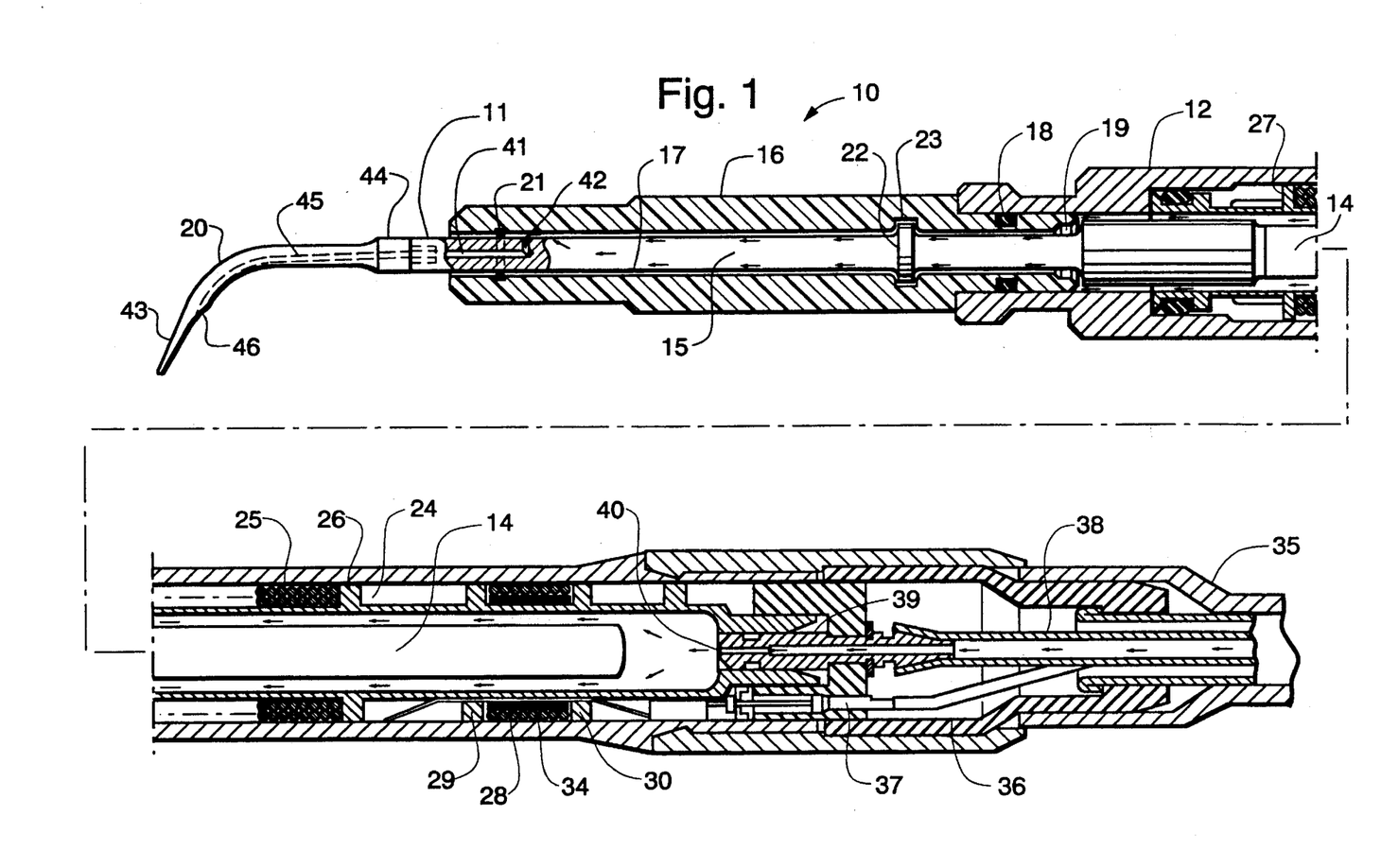
FIG. 1 is a sectional view of an ultrasonically activated tool tip of the invention as a component of a dental tool insert in combination with a handpiece.
Figure 2:
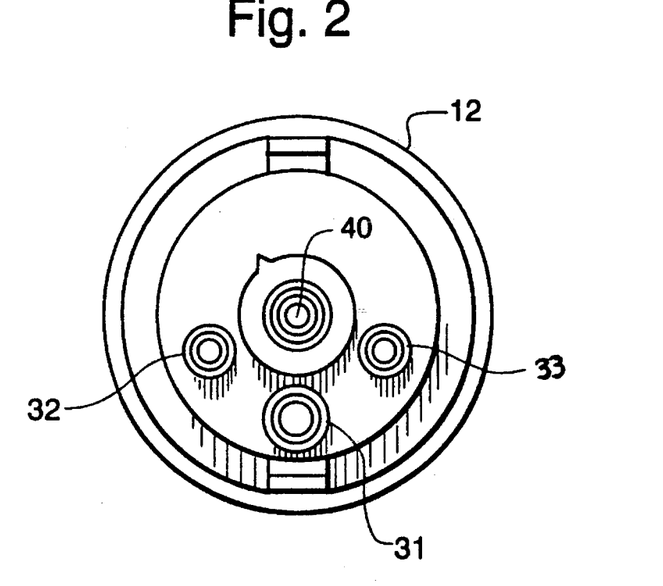
FIG. 2 is an end view of the handpiece component with the electrical/fluid supply connectors detached.

Referring to the drawings, FIG. 1 and 2 show a preferred embodiment of the invention wherein the tip is a component of an ultrasonically activated tool 10 for dental use, comprising a dental tool insert 11 in combination with a handpiece 12.

The general configuration of the tool of the invention is well known in the art and is similar to the ultrasonic device described by Perdreaux in U.S. Pat. No. Re. 30,536.

The tool insert 11 includes a tool tip 20, a key element of the invention which will be described in more detail below, and a magnetostrictive element 14, joined by a connecting body 15. A portion of the connecting body 15 is enclosed in a sleeve 16 which is formed to enclose a portion of the connecting body 15 such that the connecting body is free to transmit energy to the tip. In addition, the sleeve forms an annular passageway 17 permitting fluid flow to the tip 20. A reduced end cross-section of the sleeve 16 permits it to be removably inserted into the housing 12. An O-ring 18 fits into a groove cut into the sleeve providing a retaining, frictional fit therebetween. The internal posterior face 19 of this section is countersunk to facilitate fluid flow about the connecting body. At the distal end of the sleeve, its internal bore is fitted with a groove and O-ring 21 which, in combination with the connecting body 15, provide a seal for preventing fluid from flowing from the assembled sleeve and connecting body.

The connecting body 15 functions as an acoustical impedance transformer for transporting energy from the magnetostrictive stack 14 to the work tool tip 20. As is well known in the art, the connecting body 15 varies in cross-section along its longitudinal length which varies the amplitude of mechanical vibration, with the ultimate object of obtaining a desired amplitude magnification at the operating tip that is useful for performing a task on a workpiece. These principals are well described by Banko in U.S. Pat. No. 3,930,173, which is incorporated herein by reference. As described by Banko, the cross-section and, hence, mass of the various portions of the connecting body are designed to appropriately locate nodes and loops of longitudinal vibration. As noted therein a nodal point is where the amplitude of longitudinal vibration is zero and internal stress in the connecting body is greatest while a loop is a point where longitudinal motion is at its greatest and stress the least. Thus, it is desirable to locate supporting and sealing O-rings and the like at nodal points.

The connecting body 15 includes a ring 22 brazed or machined onto its shaft adjacent to the nodal point and sized to fit loosely into a corresponding groove 23 cut into the sleeve interior surface. The ring 22 includes a single key (not shown) on its outer circumference that fits into one of two semicircular bypasses (not shown) cut longitudinally into the interior surfaces of the bore, 180° apart from each other and centered with a radius or altitude of the groove 23. The key is held in one of the bypasses after assembly which serves as a retainer for the key while the other bypass provides a path for fluid flow around the ring.

Brazed or otherwise firmly attached to the connecting body 15 is the magnetostrictive vibrator or stack 14 which is preferably formed of a metal alloy such as permanickel, nickel or other alloys that possess high tensile strength and are highly magnetostrictive in character.

The housing or handpiece 12 includes a coil unit 24 that produces a magnetic field for inducing motion longitudinally to the insert 11 through the magnetostrictive stack 14. The coil unit includes a drive coil 25 that is connected to an alternating current source. The drive coil 25 is wound in a double coil between retaining flanges 26, 27 and provides an electromagnetic field in the handpiece 12. A feedback coil 28 of fine wire is provided to register voltage developed by the insert in the electromagnetic field and the handpiece. The feedback coil is a winding of five layers of wire, between flanges 29, 30, and is connected to ground terminal 31 and terminal 32, shown in FIG. 2. A bucking coil 34, of heavier wire than the feedback coil is wound in one layer over the feedback coil and is designed to minimize transformer coupling between the drive coil and the feedback coil. The bucking coil and drive coil are connected between terminals 31 and 33 in one continuous wire. The drive coil is attached to terminal 33 and, using a right hand turn for example, is wound from flange 26 to flange 27 and back. The end of the wire is then connected to terminal 31. The bucking coil and drive coil are wired in series and are wound in opposite direction and are therefore electromagnetically 180 degrees out of phase. The bucking coil is electrically insulated from the feedback coil.

Electrical power and fluid are supplied to the instrument by means of a cable 35, including a plug attachment 36 that connects to the handpiece. The electrical supply is connected through three electrical pin connectors 37 (only one shown) that mate with the handpiece receptacle terminals shown in FIG. 2. Pin connectors connected to the terminals 32, 33 provide power to the coil and register feedback while a pin connected to a grounded terminal 31 acts as a common ground. The cable 35 also includes a fluid conduit 38 and a connector fitting 39 for attachment to the body of the handpiece. The conduit supplies fluid to the handpiece, and, ultimately, the tool tip 20, through a passageway 40, initially into contact with the magnetostrictive element 14 to provide cooling.

At the distal end of the connecting body 15, the connecting body is counter-bored to form a central axial longitudinal passageway 41 for fluid flow to the tip 20. A radial boring 42 in the connecting body 15 at the interior terminus of the fluid passageway boring connects the central passageway 41 with the interior of the sleeve 16 to collect fluid flowing from (shown in the drawings as small arrows) about the magnetostrictive element. The radial boring 42 is located on the internal side of the O-ring gasket 21 so that flow of fluid from the handpiece interior is only from the central bore 41 out of the connecting body.

The tip 20, the operative portion of the ultrasonically activated tool, comprises a distal tip portion 43 for contacting workpiece surfaces and a shank portion 44 that is secured to the connecting body 15. The connecting body includes a counter bore for receiving the tip shank 44 which may be secured by brazing, mating threads or the like. A fluid passageway 45, described in detail below, formed interior to the tip element or body, exits through a internal or side wall in the tip to provide a fluid discharge orifice 46.

Figure 3:
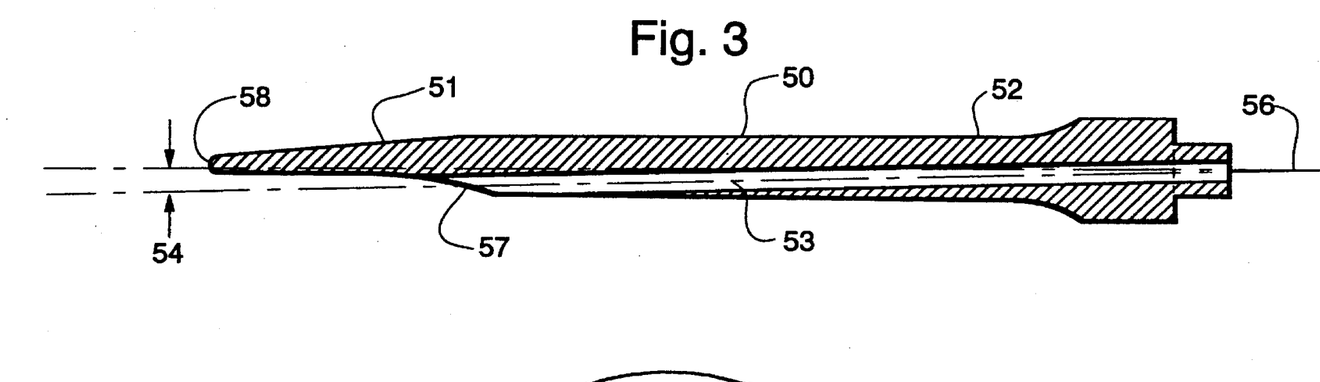
FIG. 3 is an enlarged sectional view of a tip of the invention having an angularly offset fluid passageway.
Figure 4:
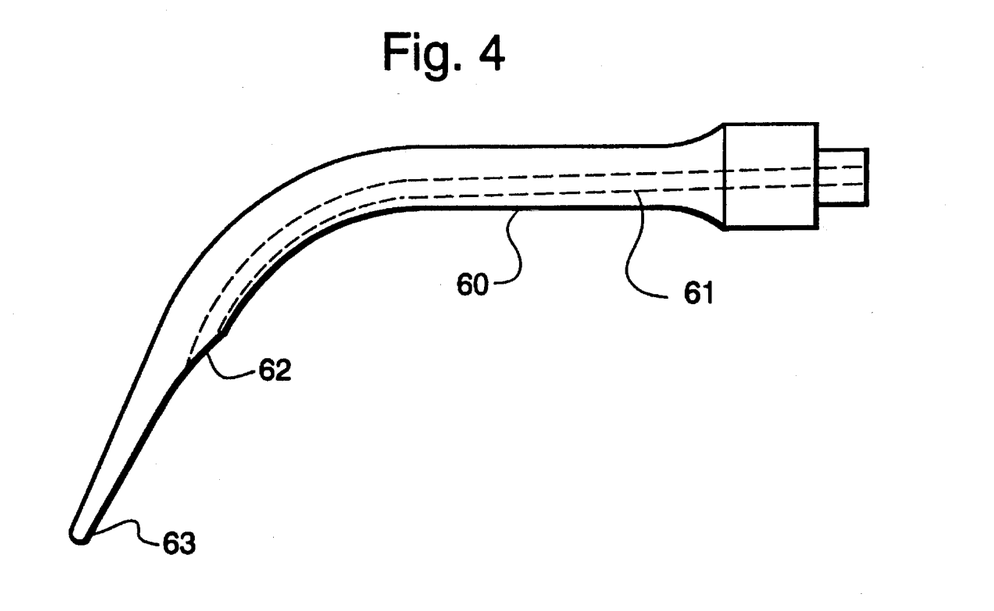
FIG. 4 is an elevational view of a tip similar to FIG. 3 that has been shaped for a particular preferred dental use.

Referring to FIGS. 3 and 4, preferred embodiments 50, 60 of the invention are shown. FIG. 3 is a sectional elevational view of a tool tip 50, before shaping for contacting workpiece surfaces. In general, while a straight tool shape may find application and is within the scope of the invention, the tool tip 50 of the invention is further formed by bending into a tool tip 60 having a shape such as that shown in FIG. 4, which shape is useful in particular applications for which the tool is employed. Referring to FIG. 3, the tool comprises a distal tip end 51 that is specially tapered and shaped to conform to workpiece surfaces with which it is to be contacted. The tip further includes a shank 52 that includes a reduced end that is received, as noted above with respect to FIG. 1, by a counter bore on the connecting body 15. A fluid passageway 53 is bored through the body of the tip, with an angular offset 54 from the longitudinal center axis 56 of the tip body such that fluid discharge orifice 57 is formed in a side wall of the tip body, located a selected distance from the distal end 58 of the tip. A key element of the invention is the relationship between the location of the center axis of the passageway discharge orifice 57 and the distal tip end 58.

Boring of the fluid passageway 53, begins at the center axis 56 of the shank 52 and is angularly offset from the tip center axis, preferably by less than 3°, such that the fluid discharge orifice preferably exits about 2–8 mm from the tip end 58. As a result, the end portion 51 of the tip is remarkably and uniquely strong and may readily be tapered and shaped to a useful, narrow point. Additionally, the location of the discharge orifice 57 is such that it is located adjacent to a vibrational node of relatively low motion which minimizes spray and mist formation.

The exact location of the fluid discharge orifice 57 and, hence, the angle offset 54 employed in boring the passageway 53 is determined by the ultimate final shape of the tip and the flexural motion desired.

Where the shape of the tip deviates from the linear profile of FIG. 3, such as those shown in FIG. 4–6, a bending force is introduced to the longitudinal vibration of the insert. This bending force causes a flexural, resonant vibration in the bent or formed end 58 of the tip, at approximately right angles to the axis of the bent tip, as described below.

In flexural resonance, a rod-like piece of metal such as the tip insert of interest will vibrate by bending back and forth. The rate, or frequency, with which it vibrates is determined by its physical characteristics. The lowest frequency of vibration is that in which the overall length of the rod is one half wave length long. The rod bends back and forth about its mid-point, or node, with the ends moving at right angles to the axis of motion. There is no motion at the node, while loops of maximum motion exist at the ends. The lowest frequency of flexural vibration, where the length of the rod is one half wave long, is termed the fundamental frequency. As noted above with respect to the connecting body, at the ends of such a vibrating rod, where the motion is at a maximum, the stresses in the metal of the rod are zero, while at the node, where the motion is zero, the stresses are at a maximum. Because of these stresses, maximum motion or strain, is limited by the ultimate and fatigue strengths of the material of which the rod is made.

The rod may also vibrate at "harmonic frequencies", or integral multiples of the fundamental frequency. Then there will be as many nodes (points of zero flexural motion), as is the number of the harmonic. For example, at the fifth harmonic frequency, (five times the fundamental frequency) there will be five nodes and six loops.

If the rod is of uniform cross-section, material, and shape, the location of nodes and loops will also be uniform, and distributed along the length. If cross-sections and materials change along the length of the rod, constituting a varying mass axis, the distribution of loops and nodes changes, generally in inverse ratio to cross-sectional dimensions. If the "mass axis", that is, the center of mass distribution along the physical length of the rods, is linear and longitudinal vibration is induced, no flexure occurs.

In the insert 11 of the invention, the materials and the cross-section vary, both in shape and area, along its longitudinal length. These differences do not prohibit resonant vibration, either longitudinal or flexure, but do affect the locations and amplitudes of nodes and loops. Bending or shaping the tip into a useful shape for contacting a particular workpiece, such as dental cavities or tooth surfaces, causes a displacement of mass at or near the distal end of the tip. This displacement causes the flexural vibration in the tip to occur at the frequency of the insert. The tip is shaped to provide necessary amplification of flexural motion vibration and to allow useful access to various areas of the teeth.

The flexural mode of vibration generates loops and nodes from the end of the tip to the opposite end of the insert. However, because the cross-sectional area or mass axis of the insert increases greatly as the distance from the tip increases, the magnitude of the flexural vibration at the loops decreases to a fraction of that generated at the tip. For conventional tips, described above, as the tip fluid flow for cooling the insert and workpiece area flows over the vibrating tip towards the working, distal end portion of the tip, the fluid must pass loops of flexural vibration that exist at the end of the insert. In many conventional tips, the motion at the loops near the tip is relatively large, which it must be to provide active workability, and the fluid immediately leaves the tip as a mist, spray, or aerosol, preventing the fluid from reaching the tip, where it is needed.

The preferred tip 60 of FIG. 4 overcomes this difficulty by boring the internal fluid passageway 61 through the tip at an angular offset from the longitudinal center axis of the tip body as shown in FIG. 3 such that the passageway emerges from the shaped tip as a fluid discharge orifice 62 at or very near the first node of vibration. At 25 kHz and 30 kHz, the FIG. 4 tip design, produces its first node at from about 4 to 5 mm from the tip. The second loop, after the loop at the tip end 63, occurs between 7 and 9 mm from the tip end 63, where the flexural motion is still great enough to cause complete misting of the fluid flowing towards the tip.

The fluid passageway in the most preferred tip is angularly offset such that it breaks out of the tip wall between about 5.5 and 6.5 mm from the tip end 63. The supply of fluid emerging from the discharge orifice 62 exits at a point where the vibrational motion is reduced to a level that will not cause misting or spraying. Upon discharge, the velocity of the emerging fluid carries the fluid principally along the concave surface of the tip to the tip distal end 63. Here, motion is again maximized. While spraying occurs, the spray is at the work surface and will properly flush and cool the surface of the tooth.

As noted above, the tip 60 shown in FIG. 4 is a preferred embodiment of the invention, finding universal usefulness in the dental field for use as a cleaning, scaling and general all purpose tool, having desirable flexural activity, good wear qualities and minimal spray interference. The shape of the tip 60 shown in FIG. 4 is produced by a means of a single bend. The tip is bent through an arc of about 60°–70° degrees, typically made after the passageway has been bored. Thus, care must be undertaken to insure that the bend does not restrict flow of fluid through the tip. The exact shape of the tip will be determined by the workpiece surfaces upon which the tool will be utilized.

Figure 5:
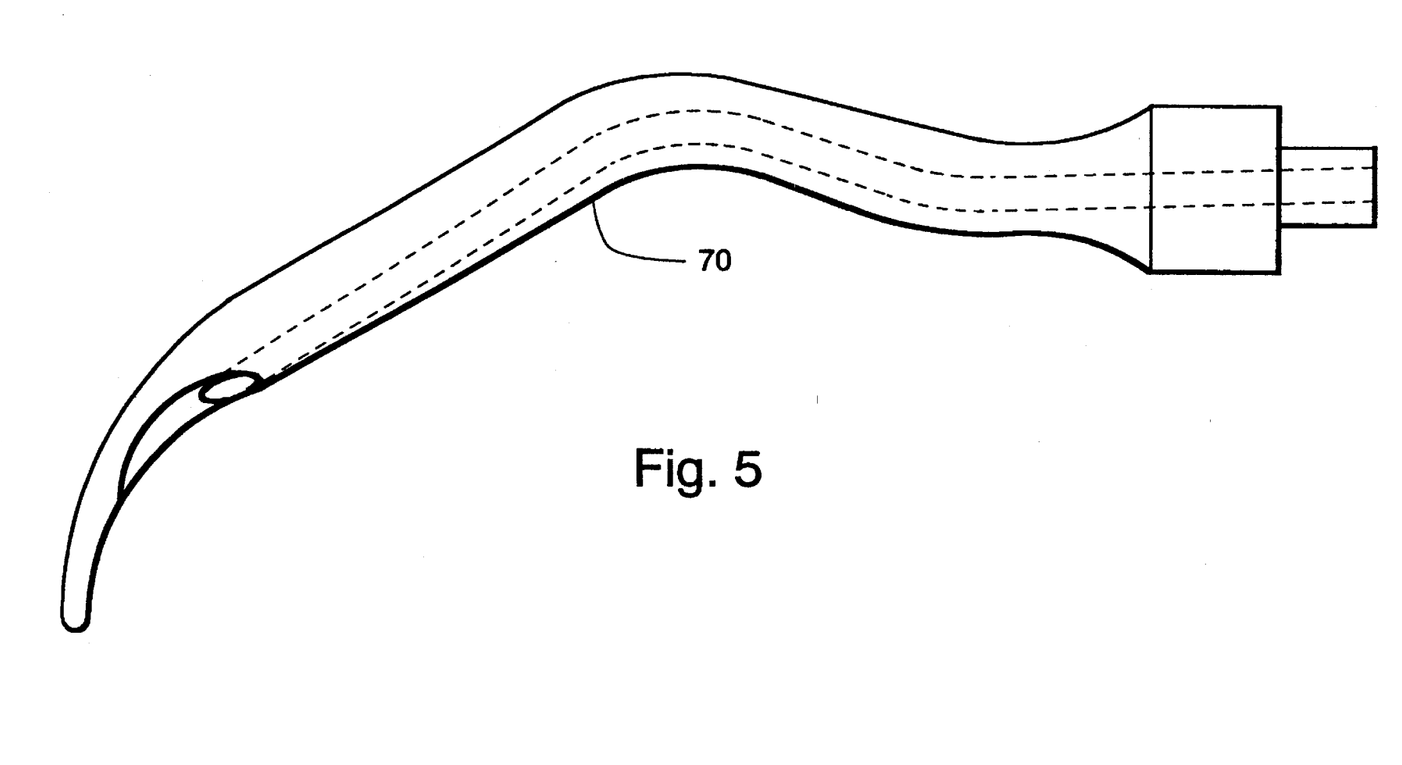
FIG. 5 is another embodiment of FIG. 3, shaped for another preferred dental use.
Figure 6:
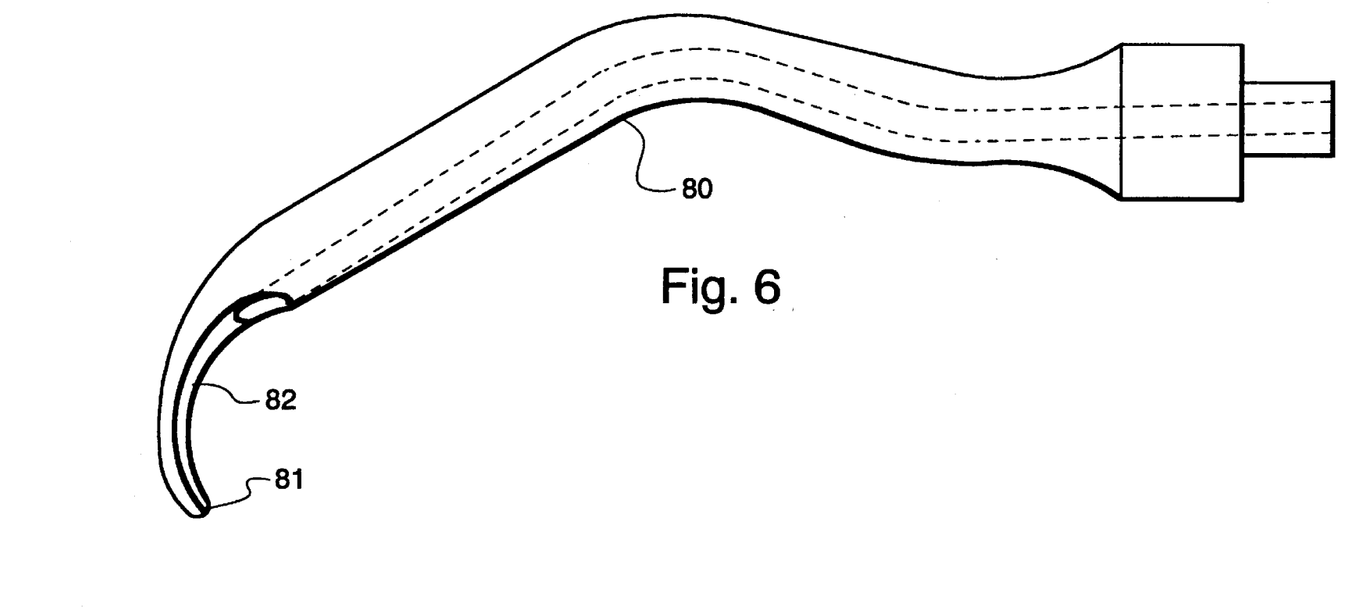
FIG. 6 is a modified embodiment of FIG. 5 of the invention.

FIGS. 5 and 6 show other embodiments 70, 80 of the tip of the invention, also useful for dental applications, having shapes different from the tip 60 of FIG. 4. In FIGS. 5-6, three bending radii are evident and employed to determine the shape of the tip. In FIG. 6, a further bend is made at the distal end 81 of the tip 80 and a portion of the tip is removed to form a channel 82 for assisting and directing the fluid flow onto the workpiece in a particular manner.

It is recognized in the field of dental instruments and the like that the particular shape employed and an exact orifice discharge configuration are a function of the workpiece or operation to be performed. The most useful or optimal shapes are often empirically determined by those skilled in the art. A key element of the present invention is the establishment of the relationship between the distal end of the working tip and the location of the orifice discharge such that the orifice is located sufficiently distant from the distal end yet sufficiently close to direct fluid onto the tip and workpiece. The location of the discharge orifice must be such that the tip body remaining after machining to effective dimensions is strong. Secondly, the orifice located must be such that the fluid flow does not cause excessive spray and misting that interfere with efficient operation of the tool.

Figure 7:
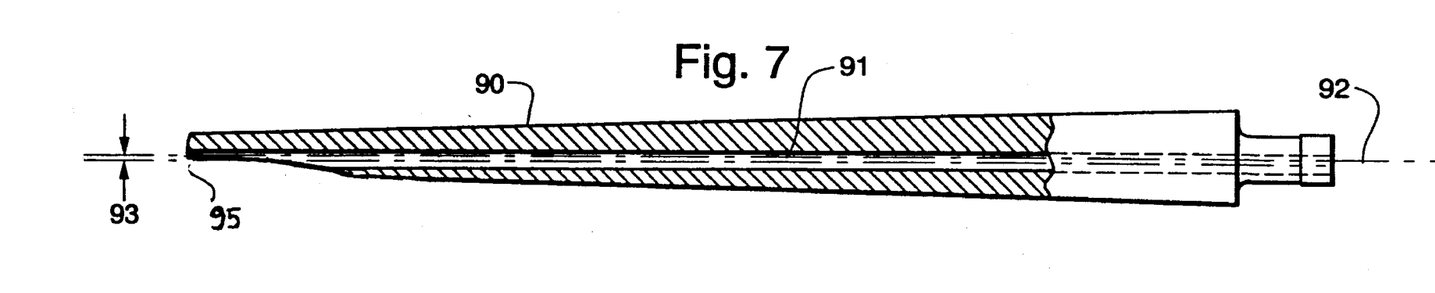
FIG. 7 is an enlarged sectional view of a tip of the invention having an eccentric offset fluid passageway.
Figure 8:
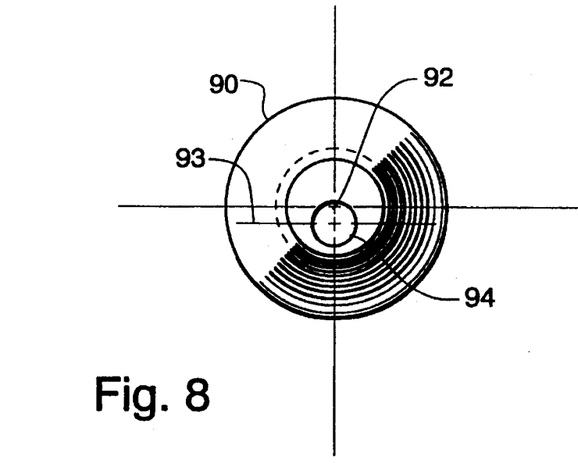
FIG. 8 is an end view of the distal end of the tip of FIG. 7 showing the fluid discharge orifice.

Another embodiment of the invention is shown in FIGS. 7 and 8. In tip 90, shown in FIG. 7, a fluid passageway 91 is drilled through the body substantially in parallel with the center axis 92 of the tip body but a slightly parallel or eccentric offset 93 therefrom of a selected dimension therefrom. The fluid discharge orifice 94 is eccentric to center axis 92 of the tip, as shown in FIG. 8. As shown in FIG. 7, the tip end portion 95 is machined such that the discharge orifice position may be adjusted as desired, here displaced from the tip end. As is the case with most tool tips, the tip 90 employing the FIG. 7 embodiment will most likely be formed into a curved shape to impart desired flexural motion and to conform to desired workpiece shapes. The FIG. 7 embodiment maintains the advantage of retaining more metal for flexural strength and wear resistance on the convex side of the tip which might be bent to any configuration, such as those shown in FIGS. 4-6.

Referring to FIG. 1, in operation, an alternating current impressed upon the coil unit 24 described above creates an alternating magnetic field in the handpiece portion 12 surrounding the magnetostrictive stack 14. The electro-magnetic field vibrationally excites the magnetostrictive stack 14, imparting longitudinal motion at ultrasonic frequency to the connecting body 15 and tip 20 connected thereto. As discussed above, the longitudinal motion causes the distal end 43 of the tip 20 to vibrate flexurally to produce a motion useful for performing a task on a workpiece, such as, for example, cleaning a tooth. Simultaneously, a flow of cooling/irrigating fluid flows into the handpiece chamber containing the magnetostrictive stack, cooling the stack and passing therefrom into the annular space between the sleeve 16 and connecting body 15. The fluid leaves the connecting body discharge passageway and flows into the tip passageway 45, discharging from the discharge orifice 46 onto the workpiece surfaces, providing cooling and cleaning or other desired effects depending upon the character of the fluid applied and workpiece operated on.

It is clear from the invention that the nature of the device activating the tool longitudinally is not a limitation. The tool may be electronically activated by means of electro-magnetostrictive elements as discussed or piezo electric crystals or other means, including air or water activation. While the preferred embodiment of the invention focuses upon use of the tool for dental operations, such as cleaning and scaling, it is intended that the instrument have broad use and application wherever it is desirable to act on a workpiece surface with a vibratory motion with simultaneously providing fluid to irrigate the tip and workpiece surfaces. The exact dimensions of the tip are determined by the operation for which the tip is employed. A typical tip shank diameter is 0.065 inches (1.65 mm) for certain dental application, such that the tip end can be tapered to a diameter small enough to fit into narrow crevices and areas between teeth. The exact location of the discharge orifice of the fluid is determined by many factors, including the frequency of operation as well as the transducer employed.

The nature of the fluid delivered to the workpiece is dependent upon the operation to be performed on or at the workpiece. In a dental cleaning environment, water is a useful fluid for cooling and removal of debris. In other uses it may be preferred to employ a saline solution, sterile water or a solution containing some selected medicament to achieve a particular purpose.

The nature of the passageway drilled within the tip is not critical. Conventionally, it will be a straight, linear bore. However, it is within the scope of the invention if a bore is curved. The essence of the invention is to establish a discharge orifice that maximizes the amount of material or metal remaining at or on the tip end for flexural strength while providing an orifice location with respect to the tip motion where spray is minimized.

The tip may be formed of any material that has sufficient strength under the longitudinal and flexural stresses to which it is subjected. Typically, a high strength stainless steel is utilized but the tip may be formed of engineered polymerics or other materials, such as carbon-filled polycarbonate, graphite composites or other materials that have sufficient hardness and elasticity to accommodate the motional stresses and wear of the operation.

It is noted that the tool tip of the invention is depicted in cross-section as cylindrical, tapering to a relatively small diameter. It is well known in the art that tools may have other configurations and cross-sections and such tools are within the scope of the invention. Whether the resulting tool tip is rectangular, irregular shaped or some other shape in cross-section or includes some configuration other than a tapered point at the working tip, it is preferred that the discharge exit be located from the terminal end of the tip at or just before the flexural node where there is the lowest flexural motion and the orifice exit is least likely to cause fracture stresses in the tip. The invention must also be located distant from harmonic loops where motion is greatest which tend to create excessive sprays. Such a loop is typically 7-9 mm from the tip end, for this preferred embodiment of this invention.

The particular characteristics of the shape of the tip, that is, bending radii, length of bent arc, length of section beyond the bend, tip taper and the material from which the tip is fashioned, all contribute to the performance characteristics of the tip in flexure. The design of the tip, generally, and of the FIG. 4 tip in particular, utilizes the factors described above to provide a gain or amplification of the longitudinal vibrational motion produced by the insert, of from two to five fold.

The tip of the invention may be produced by a number of milling techniques. A preferred method first requires that the tip body is formed of cylindrical rod drawn to a diameter that is slightly larger than the finished tip diameter. The selected material is one that is corrosion resistant, of high tensile strength, high sheer strength, high fatigue limit, good toughness and that can be bent machined and/or formed. The rod is milled to substantially its final configuration before shaping and bending. The fluid passageway is formed in the tip body by means of a number of techniques including drilling and boring. Typically, after forming the passageway, the tip is machined, formed or bent to its useful finished shape and configuration.

A preferred boring method is by means of electric discharge machining (EDM), a process that insures that the passageway is angled to break out on a wall surface of the tip rod on the convex side of the existing or intended bend, preferably 5 to 8 mm from the end of the tip. In EDM, the passageway of a desired diameter is formed by a DC current that generates rapid repetitive spark discharges through a film of dielectric fluid flowing between the workpiece and a shaped electrode tool. An EDM system Model No. SP-1M, manufactured by Japax EDM Products, Division of Mitsui Machine Technology, Inc. of Glendale Heights, Ill., was employed to form 0.022 inch (0.56 mm) diameter fluid passageways for the tip of the invention.

Alternatively, the passageway is bored into the tip body or cylinder using a lathe that is equipped with a tail stock that can be offset. The offset is adjusted, for example, sufficient to produce an angle of 1 to 1.6 degrees from the centerline of the tip body cylinder. This is equivalent to an offset distance of 0.4 to 0.6 mm at the end of the cylinder. The passageway is drilled and the offset tailstock of the lathe is returned to its centering position, aligned with the live or driven center of the lathe. The blank is then machined, for example, to provide tapering, to its final design dimensions. The result will be a tip blank that has its internal fluid passageway centered at the large end of the blank and exiting at a cylindrical wall displaced from but near the small end of the tip. This process produces a blank that is of uniform cross-section, tapering near the end of the tip, where vibrational stresses are greatest and maximum material within the design parameter is needed for strength. Maximum strength is achieved by this method because the machine tip blank has remained concentric to its maximum strength orientation formed along its longitudinal axis during drawing. The resulting tip will have a fluid outlet located 2 to 8 mm from the end of the tip.

We claim:

1. A transducer activated tool for contacting workpiece surfaces and directing a fluid adjacent to said surfaces, comprising:
    an activated tip having distal surfaces shaped to contact said workpiece surfaces and a fluid passageway internal to tip formed generally along the longitudinal center axis of the tip but offset such that a fluid discharge orifice is formed displaced from said distal tip axis;
    an activating transducer connecting body connecting said tip to an activating transducer; and
    a fluid source connecting to said tip fluid passageway and providing a flow of fluid discharging from said tip fluid passageway discharge orifice, said passageway being formed by electric discharge machining said passageway in a cylindrical rod, beginning at the center axis of an end of said rod and continuing at an angle of less than about 3 degrees from the center axis of said rod such that the passageway forms a discharge orifice 2-8 mm from the opposite distal end of said rod.

2. The tool of claim 1 wherein said tip fluid passageway is angularly offset from the tip longitudinal center axis such that said fluid discharge orifice is formed in a lateral surface of said tip.

3. The tool of claim 2 wherein said fluid passageway is angularly offset from the center axis of the tip by less than about 3 degrees.

4. The tool of claim 2 wherein said fluid passageway is angularly offset from the centerline of the tip by less than about 2 degrees, such that the passageway orifice exits about 2–8 mm from the distal end of said tip.

5. The tool of claim 4 wherein said fluid passageway is linear with respect to said tip center axis.

6. The tool of claim 4 wherein said fluid passageway is curved with respect to said tip center axis.

7. The tool of claim 1 wherein said fluid discharge orifice is positioned such that said orifice has a center axis that is about 0.01 to about 8 mm from the distal end of said tip.

8. The tool of claim 7 wherein said fluid discharge orifice center axis that is about 5.5–6.5 mm from the distal end of said tip.

9. The tool of claim 1 wherein said activating transducer activates said tip by sonic, ultrasonic, fluid or air means.

10. The tool of claim 1 wherein said activating transducer is a piezo crystal.

11. The tool of claim 1 wherein said discharge fluid is saline, water or a solution comprising a medicament.

12. The tool of claim 1 wherein said tip is connected to said connecting body by threads, press fit, soldering, brazing or welding.

13. The tool of claim 1 wherein said distal tip surfaces are shaped for contacting dental surfaces.

14. The tool of claim 1 wherein said tip is formed of stainless steel, carbon filled polycarbonate or graphite composite material.

15. The tool of claim 1 wherein said tip shape is for a universal dental use having a distal portion bending from its centerline axis through an arc of about 60°–70° degrees.

16. The tool of claim 1 wherein said tip shape comprises one or more bends wherein said orifice exits on the inside of the bending radii adjacent the distal end of said tip.

17. The tool of claim 1 wherein said transducer ultrasonically activates said tip producing a substantial flexural motion normal to the tip longitudinal centerline axis and said fluid orifice is located near a flexural node of the tip but not adjacent a flexural or longitudinal loop thereof.

18. The tool of claim 1, said tool tip having a circular, rectangular or irregular cross-section.

19. The tool of claim 18, said tip fluid discharge orifice located on a concave surface within about 6 mm from the tool distal end.

20. The tool of claim 1 wherein said tip fluid passageway orifice is eccentrically offset from said tip axis, wherein the passageway is substantially parallel to the center axis of the tip but displaced from said axis by 0.1 to 0.5 mm.

21. The tool of claim 20 wherein said tip distal end is shaped to contact workpiece surfaces and said fluid discharge orifice is located such that said fluid impinges upon said workpiece surfaces.

22. An insert for an ultrasonically activated tool of a generally axially elongated cylindrical structure comprising a handpiece including a coil for generating an electromagnetic field, said insert being vibrated at high frequency in longitudinal motion in response to said coil, said insert comprising:
    a magnetostrictive element;
    a connecting body, axially transmitting said high frequency motion from said ultrasonic magnetostrictive element; and
    a tip, axially attached to said connecting body, that receives said longitudinal motion, having distal surfaces shaped to contact a workpiece, said tip comprising, a fluid passageway, internal to said tip, formed generally along the longitudinal center axis of said tip but offset from said axis such that a discharge orifice formed in said tip is displaced from said distal tip end center axis, said passageway being formed by electric discharge machining said passageway in a cylindrical rod, beginning at the center axis of an end of said rod and continuing at an angle of less than about 3 degrees from the center axis of said rod such that the passageway forms a discharge orifice 2–8 mm from the opposite, distal end of said rod.

23. The insert of claim 22 wherein said passageway is angularly offset from said tip axis by less than about 3 degrees.

24. The insert of claim 23 wherein said tip passageway orifice exits within a range of about 2–8 mm from the distal end of said tip.

25. The insert of claim 22 wherein said workpiece comprises dental surfaces.

26. The insert of claim 25 wherein said tip shape conforms to said dental surfaces, comprising a radius bend at the tip such that said fluid orifice is on the concave portion of said bend to direct fluid flow adjacent to said workpiece.

27. The insert of claim 22 wherein a fluid passageway is eccentrically offset from said tip axis, wherein said passageway is formed substantially parallel to the center axis of the tip but displaced therefrom.

28. The insert of claim 27 wherein said passageway is displaced from said axis by about 0.1 to 0.5 mm.

29. The insert of claim 27 wherein the discharge orifice is shaped such that the fluid flowing therefrom forms a desired pattern for contacting dental surfaces contacted by said tip.

30. A method of cleaning a workpiece, comprising:

contacting said workpiece with a transducer activated tool tip; and directing a fluid adjacent to said workpiece, said tool comprising, an activated tip having distal surfaces shaped to contact said workpiece and having a fluid passageway internal to said tip generally along the longitudinal center axis of the tip but offset such that a fluid discharge orifice is formed displaced from distal tip axis a connecting body connecting said tip to an activating transducer and a fluid source connecting to said tip fluid passageway for providing the flow of fluid discharging from said tip fluid passageway orifice, said passageway being formed by electric discharge machining said passageway in a cylindrical rod, beginning at the center axis of an end of said rod and continuing at an angle of less than about 3 degrees from the center axis of said rod such that the passageway forms a discharge orifice 2–8 mm from the opposite, distal end of said rod.

31. A method of making a transducer activated tool tip for contacting workpiece surfaces and directing a fluid adjacent to said surfaces, comprising, shaping a tip body to form distal surfaces for contacting said workpiece surfaces; and forming in said tip body a fluid passageway internal to said tip, generally along the longitudinal center axis of the tip but offset therefrom such that a fluid discharge orifice is formed displaced from said distal tip center axis, said passageway being formed by electric discharge machining said passageway in a cylindrical rod, beginning at the center axis of an end of said rod and continuing at an angle of less than about 3 degrees from the center axis of said rod such that the passageway forms a discharge orifice 2–8 mm from the opposite, distal end of said rod.

32. The method of claim 31 wherein shaping of said cylindrical rod into a desired shape for contacting workpiece surfaces comprises machining and bending such that said fluid orifice is on a concave surface thereof to direct fluid adjacent or onto said workpieces.

33. The method of claim 31 wherein forming said tip fluid passageway, comprises:

securing a cylindrical rod in a lathe such that the tail end of said rod opposite said rod distal surfaces is offset from the longitudinal center axis of the lathe; and boring said rod such that said passageway forms a fluid discharge orifice 2–8 mm from the distal end of said tip.

\* \* \* \* \*